(12) United States Patent
Nord et al.

(10) Patent No.: US 8,961,382 B2
(45) Date of Patent: Feb. 24, 2015

(54) METHOD AND APPARATUS PERTAINING TO RADIATION-TREATMENT PLAN OPTIMIZATION

(75) Inventors: Janne Nord, Espoo (FI); Perttu Niemelä, Helsinki (FI); Esa Kuusela, Espoo (FI)

(73) Assignee: Varian Medical Systems International AG, Cham (CH)

( * ) Notice: Subject to any disclaimer, the term of this patent is extended or adjusted under 35 U.S.C. 154(b) by 2 days.

(21) Appl. No.: 13/356,835

(22) Filed: Jan. 24, 2012

(65) Prior Publication Data

US 2013/0187062 A1 Jul. 25, 2013

(51) Int. Cl.
*A61N 5/10* (2006.01)

(52) U.S. Cl.
USPC ............................................................ 600/1

(58) Field of Classification Search
USPC .......................... 600/1, 2; 378/64, 65, 68, 69; 250/492.1–492.3
See application file for complete search history.

(56) References Cited

U.S. PATENT DOCUMENTS

| 8,315,357 | B2 * | 11/2012 | Zhu et al. | 378/65 |
| 2009/0326615 | A1 * | 12/2009 | Nord et al. | 607/88 |
| 2010/0020931 | A1 * | 1/2010 | Otto et al. | 378/65 |
| 2010/0104068 | A1 * | 4/2010 | Kilby et al. | 378/65 |

* cited by examiner

*Primary Examiner* — Samuel Gilbert
(74) *Attorney, Agent, or Firm* — Fitch, Even, Tabin & Flannery LLP

(57) ABSTRACT

A control circuit optimizes a radiation-treatment plan to provide an initially-optimized radiation-treatment plan and then modifies that initially-optimized radiation-treatment plan to reduce corresponding monitor units (MU's) to provide a radiation-treatment plan that is further optimized for monitor units. This modification can comprise, at least in part, imposing a stronger smoothing constraint with respect to fluence. Optimizing a radiation-treatment plan to provide an initially-optimized radiation-treatment plan can comprise identifying at least one particular leaf pair for a multi-leaf collimator that requires a longest amount of time to move into a position that achieves a particular desired fluence and then selectively smoothing position requirements of that particular leaf pair to reduce the amount of time associated with that particular leaf pair while not also smoothing position requirements for all leaf pairs as comprise that multi-leaf collimator.

16 Claims, 2 Drawing Sheets

METHOD AND APPARATUS PERTAINING TO RADIATION-TREATMENT PLAN OPTIMIZATION

TECHNICAL FIELD

This invention relates generally to the optimization of radiation-therapy treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. For example, many treatment plans provide for exposing the target volume to possibly varying dosages of radiation from a number of different directions. Arc therapy, for example, comprises one such approach.

Such treatment plans are often optimized prior to use. (As used herein, "optimization" will be understood to refer to improving a candidate treatment plan without necessarily ensuring that the optimized result is, in fact, the singular best solution.) Though important to the use of treatment plans, typical optimization processes are computationally intensive. This, in turn, can require the use of expensive processing platforms and/or a considerable amount of processing time. Such burdens, however, can lead to unwanted costs and/or delay for the service provider and/or the patient.

BRIEF DESCRIPTION OF THE DRAWINGS

The above needs are at least partially met through provision of the method and apparatus pertaining to radiation-treatment plan optimization described in the following detailed description, particularly when studied in conjunction with the drawings, wherein.

Figure 1:
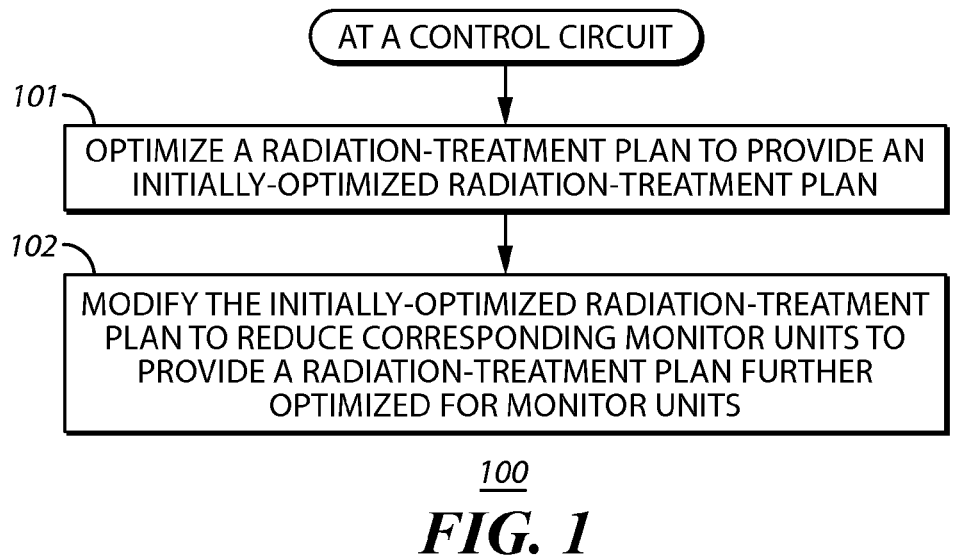
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit optimizes a radiation-treatment plan to provide an initially-optimized radiation-treatment plan and then modifies that initially-optimized radiation-treatment plan to reduce corresponding monitor units (MU's) to provide a radiation-treatment plan that is further optimized for monitor units. By one approach, for example, this modification can comprise, at least in part, imposing a stronger smoothing constraint with respect to fluence.

By one approach, if desired, optimizing a radiation-treatment plan to provide an initially-optimized radiation-treatment plan can comprise identifying at least one particular leaf pair for a multi-leaf collimator that requires a longest amount of time to move into a position that achieves a particular desired fluence and then selectively smoothing position requirements of that particular leaf pair to reduce the amount of time associated with that particular leaf pair while not also smoothing position requirements for all leaf pairs as comprise that multi-leaf collimator.

By one approach, if desired, in lieu of the foregoing or in combination therewith, optimizing the radiation-treatment plan to provide the initially-optimized radiation-treatment plan can comprise optimizing the radiation-treatment plan without considering monitor units associated with that radiation-treatment plan. In any event, modifying the initially-optimized radiation-treatment plan can comprise using an objective function as corresponds to the initially-optimized radiation-treatment plan. The latter can comprise, for example, comparing an objective function result for a modified radiation-treatment plan against an objective function result for the initially-optimized radiation-treatment plan. The purpose of this comparison need not serve to assess whether the modified plan is better, objectively, than the initial plan so much as to assess whether the modified plan is not too much worse than the initial plan.

So configured, for example, such an optimization approach permits development of a radiation-treatment plan without consideration for MU performance and then flexibly considering changes to the plan to assess whether MU delivery can be reduced without unduly sacrificing the plan's performance. By one approach, MU's can be reduced by smoothing the fluence with a stronger smoothing constraint on the fluence. The effects of altering smoothing constraints can be difficult to predict and there is no certainty that a given therapeutic result will obtain with less than delivery of a given amount of MU's. Bifurcating MU optimization from at least some other optimization activity makes it easier to assess whether any benefit in fact can be achieved in these regards.

These and other benefits may become clearer upon making a thorough review and study of the following detailed description. Referring now to the drawings, and in particular to FIG. 1, an illustrative process 100 to facilitate optimizing a radiation-treatment plan that is compatible with many of these teachings will now be presented. This process 100 can be carried out by a control circuit of choice as discussed below in more detail.

At step 101 this process 100 provides for optimizing a radiation-treatment plan to thereby provide an initially-optimized radiation-treatment plan. By one approach, for example, this can comprise optimizing that radiation-treatment plan without considering monitor units associated with the radiation-treatment plan. As used herein it will be understood that a monitor unit (MU) is a measure of machine output of a linear accelerator in radiation therapy. (Linear accelerators are typically calibrated to give a particular absorbed dose under particular conditions. By way of example, one standard calibration specifies that 100 MU's gives an absorbed dose of 1 Gray (or 100 rad) at a depth of 5 cm in a tissue-equivalent phantom for a 10×10 $cm^2$ field at 95 cm source-to-surface distance.)

That said, this process 100 is highly flexible in practice and will accommodate any of a wide variety of optimization approaches. By one approach, this step 101 will even accommodate using different optimization approaches to yield a plurality of candidate initially-optimized radiation-treatment plans.

Figure 2:
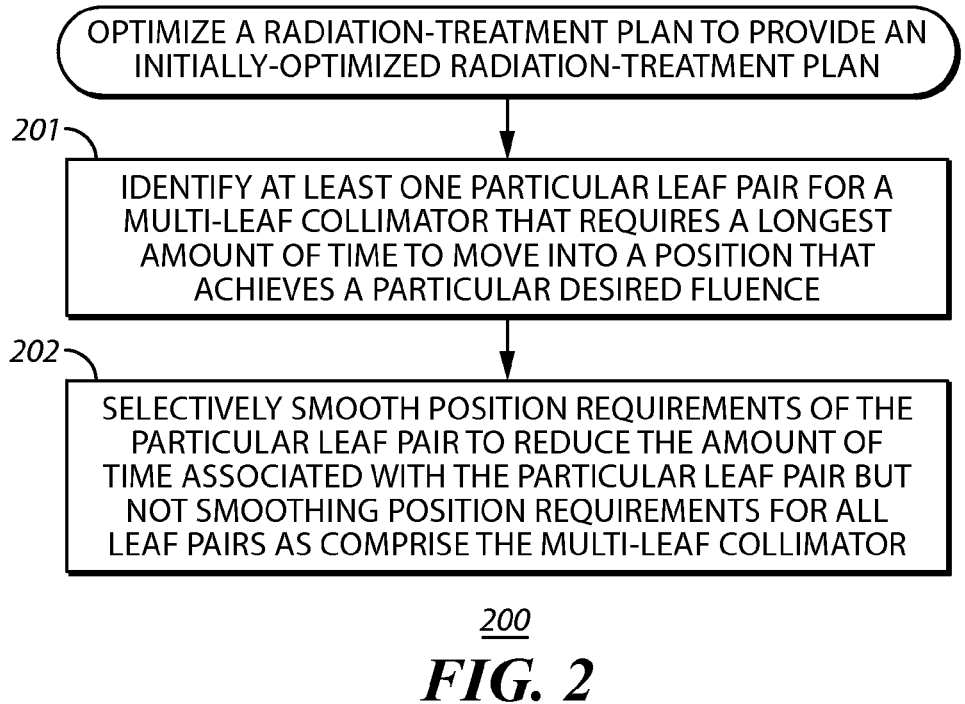
FIG. 2 comprises a flow diagram as configured in accordance with various embodiments of the invention.

Without intending any limitations in these regards, FIG. 2 provides an illustrative example of one approach in these regards. At step 201 of this process 200 to optimize a radiation-treatment plan to thereby provide an initially-optimized radiation-treatment plan, the control circuit identifies at least one particular leaf pair for a multi-leaf collimator that requires a longest amount of time to move into a position that achieves a particular desired fluence. Fluence, of course, represents radiative flux integrated over time and comprises a fundamental metric in dosimetry (i.e., the measurement and calculation of an absorbed dose of ionizing radiation in matter and tissue).

Multi-leaf collimators are known in the art and are typically comprised of a plurality of individual parts (known as "leaves") that are formed of a high atomic numbered material (such as tungsten) that can move independently in and out of the path of the radiation-therapy beam in order to selectively block (and hence shape) the beam. A typical radiation-treatment plan that employs one or more multi-leaf collimators typically specifies varying aperture positions, shapes, and sizes over the course of the treatment and this step 201 takes into account the fact that not all leaf pairs are necessarily equally tasked or challenged in these regards in a given radiation-treatment plan.

Figure 3:
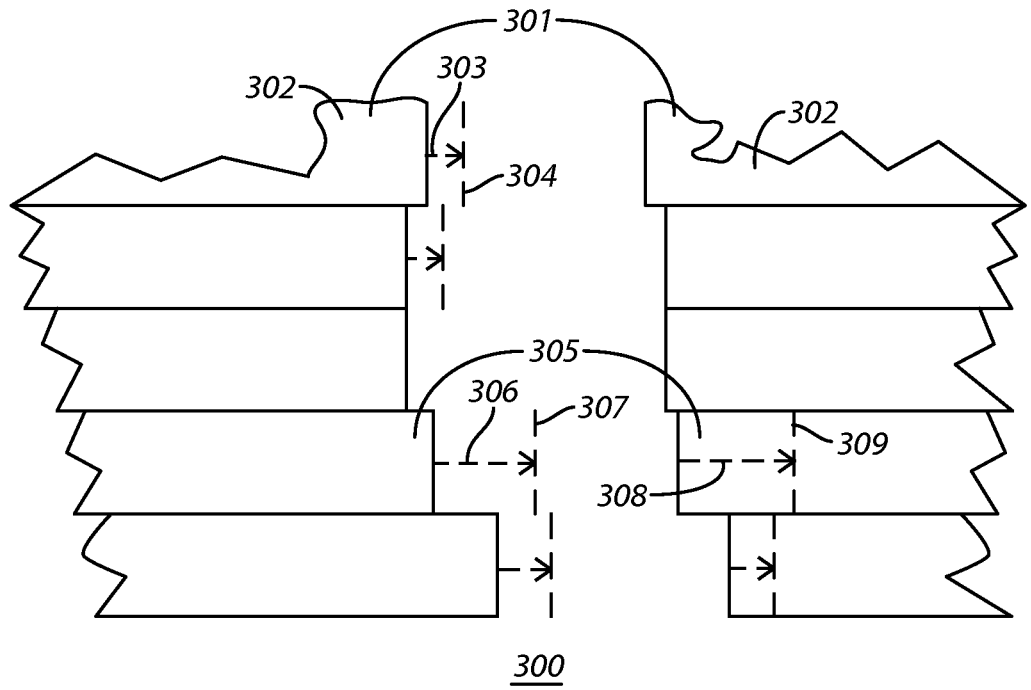
FIG. 3 comprises a front-elevational detail view as configured in accordance with various embodiments of the invention.

To illustrate by way of example, and referring momentarily to FIG. 3, a given multi-leaf collimator 300 comprises a plurality of leaves 302 that are organized as leaf pairs 301. Each leaf 302 can move in a parallel direction with respect to the other leaves (i.e., horizontally in the illustrated orientation), hence giving rise to a variety of sizes and locations for resultant space/aperture (if any) between the leaves 302.

In this illustrative example the radiation-treatment plan at issue provides for moving some of these leaves 302 to form a new aperture. The left-side leaf of the uppermost leaf pair, for example, is slated to move to the right an amount indicated by reference numeral 303 to assume a new position denoted by reference numeral 304. By way of contrast, both leaves of the leaf pair denoted by reference numeral 305 are scheduled to move to the right. More specifically, the left-side leaf is to move the distance denoted by reference numeral 306 to the position denoted by reference numeral 307 and the right-side leaf is to move the distance denoted by reference numeral 308 to the position denoted by reference numeral 309.

In this example, either leaf of the latter leaf pair 305 is to move a distance that is greater than the distance to be moved by any other leaf. Presuming that the multi-leaf collimator 300 moves each leaf 302 at a same, consistent speed, it can be readily concluded that moving the leaves of this particular leaf pair 305 will take the longest period of time as these leaves have the longest distance to move. In such a case, the aforementioned step 201 of identifying the leaf pair that requires a longest amount of time to move into a position that achieves a particular desired fluence would identify this particular leaf pair 305.

Referring again to FIG. 1, at step 202 this process 200 provides for now selectively smoothing position requirements of that particular leaf pair to reduce the amount of time associated with the particular leaf pair but not also smoothing position requirements for all leaf pairs as comprise the multi-leaf collimator. (These teachings will accommodate, if desired, so smoothing more than one such leaf pair. For example, such smoothing may be applied to, say, the two or three leaf pairs that require the longest amounts of time to move as described.)

Those skilled in the art will recognize "smoothing" as referring to the statistics/image processing-based processing of a given data set to create an approximating function that works to capture significant patterns within the data while not necessarily capturing noise or fine-scale structures and rapid phenomena. Generally speaking, smoothing aims to offer a general idea of relatively slow changes of value with little attention being paid to closely matching the data values per se.

Smoothing methodologies typically have one or more associated tuning parameters that serve to control the extent of the smoothing Accordingly, this step 202 of selectively smoothing position requirements can comprise, by one approach, assigning a stronger smoothing constraint to thereby reduce multi-leaf collimator aperture complexity.

In any event, and referring again to FIG. 1, at step 102 this process 100 then provides for modifying that initially-optimized radiation-treatment plan to reduce corresponding monitor units to thereby provide a radiation-treatment plan further optimized for monitor units. By one approach, this can comprise, at least in part, imposing a stronger smoothing constraint with respect to fluence.

It is not necessarily assured that this follow-on modification step 102 will, in fact, yield an acceptable alteration to the radiation-treatment plan. That is to say, it is possible that the initially-optimized radiation-treatment plan will offer a substandard result when the monitor units are reduced. Accordingly, by one approach this modification step 102 can include assessing the efficacy of the modified radiation-treatment plan to determine whether (or when) the delivered therapeutic results remain within some acceptable range.

By one approach this assessment can comprise using one or more objective functions as correspond to the initially-optimized radiation-treatment plan. This objective function can comprise, for example, a numerical value that represents the calculated efficacy of a given plan (such as an integer between, say, "1" and "10" where higher-valued numbers indicate increased efficacy). In such a case, this assessment can comprise, at least in part, comparing an objective function result for a modified radiation-treatment plan against an objective function result for the initially-optimized radiation-treatment plan.

By way of illustration, this can comprise calculating a threshold limit based upon that objective function result as corresponds to the initially-optimized radiation-treatment plan. The objective function result as corresponds to a given modified radiation-treatment plan can then be compared against that threshold limit to assess the acceptability of the MU-reduced modified radiation-treatment plan.

As a further illustrative example in these regards, a given initially-optimized radiation-treatment plan may have a corresponding objective function result of, say, "9." A threshold limit can be determined by subtracting a set value (such as "1") from that objective function result (to hence calculate, in this example, a threshold limit of "8"). A first modified radiation-treatment plan may have a corresponding objective function result of, say, "5." "5" is less than the threshold limit of "8" and accordingly that modified radiation-treatment plan would be rejected as unacceptable.

A second modified radiation-treatment plan, however, might have an objective function result of "8." As this objective function result is not less than the threshold limit, this second modified radiation-treatment plan could be deemed acceptable. In this case, then, a resultant optimized radiation-treatment plan would have an acceptable therapeutic profile while also exposing the patient to reduced monitor units as compared to the initial optimized radiation-treatment plan.

Figure 4:
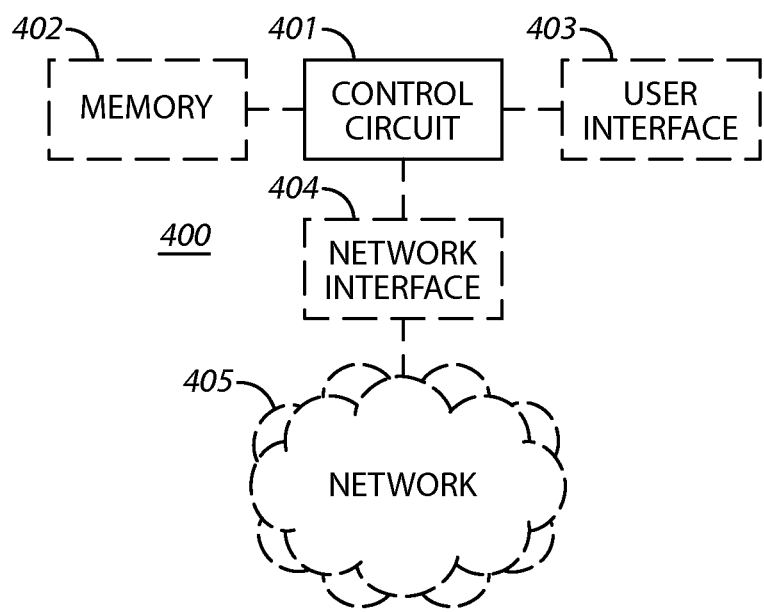
FIG. 4 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 4, an illustrative approach to such an apparatus 400 will now be provided.

In this illustrative example the apparatus 400 comprises a control circuit 401. Such a control circuit 401 can comprise, for example, a fixed-purpose hard-wired platform or can comprise a partially or wholly-programmable platform such any of a wide variety of computers. All of these architectural options are well known and understood in the art and require no further description here. This control circuit 401 is configured (for example, by using corresponding programming as will be well understood by those skilled in the art) to carry out one or more of the steps, actions, and/or functions described herein.

By one optional approach this control circuit 401 operably couples to a memory 402. This memory 402 may be integral to the control circuit 401 or can be physically discrete (in whole or in part) from the control circuit 401 as desired. This memory 402 can also be local with respect to the control circuit 401 (where, for example, both share a common circuit board, chassis, power supply, and/or housing) or can be partially or wholly remote with respect to the control circuit 401 (where, for example, the memory 402 is physically located in another facility, metropolitan area, or even country as compared to the control circuit 401).

This memory 402 can serve, for example, to non-transitorily store the computer instructions that, when executed by the control circuit 401, cause the control circuit 401 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

By another optional approach (in lieu of the foregoing or in combination therewith) the control circuit 401 operably couples to a user interface 403. This user interface 403 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

And by yet another optional approach, the control circuit 401 operably couples to a network interface 404 to thereby access one or more communications networks 405 (such as, but not limited to, the Internet or other extranets as well as local networks of various kinds). This network interface 404 can comprise any of a variety of wireless and/or non-wireless interfaces as are known in the art. As the present teachings are not particularly sensitive as to the selection of any particular approach in these regards, further elaboration here regarding such network interfaces will not be provided here.

Such an apparatus 400 may be comprised of a plurality of physically distinct elements as is suggested by the illustration shown in FIG. 4. It is also possible, however, to view this illustration as comprising a logical view, in which case one or more of these elements can be enabled and realized via a shared platform. It will also be understood that such a shared platform may comprise a wholly or at least partially programmable platform as are known in the art.

So configured, an acceptable optimized radiation-treatment plan may be further improved by reducing the planned exposure of radiation to the patient while at least substantially maintaining the planned efficacy of that radiation-treatment plan. To the extent that the value of the treatment cannot be satisfactorily maintained when reducing the amount of radiation exposure these teachings will accommodate using the original optimized radiation-treatment plan without that reduction.

These teachings are highly flexible in practice and can be applied with any of a variety of radiation-treatment planning methodologies and treatment-delivery platforms. As these teachings provide for consideration of an already-optimized radiation-treatment plan, utilization of these teachings will not typically add much in the way of further processing or computational requirements and hence can be economically and effectively utilized in practice.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

We claim:

1. A method to facilitate optimizing a radiation-treatment plan, the method comprising:
   by a control circuit:
   optimizing a radiation-treatment plan to provide an initially-optimized radiation-treatment plan by, at least in part:
   identifying at least one particular leaf pair for a multi-leaf collimator that requires a longest amount of time to move into a position that achieves a particular desired fluence; and
   selectively smoothing position requirements of the particular leaf pair to reduce the amount of time associated with the particular leaf pair but not smoothing position requirements for all leaf pairs that comprise the multi-leaf collimator; and
   modifying the initially-optimized radiation-treatment plan to reduce monitor units to provide a radiation-treatment plan further optimized for monitor units.

2. The method of claim 1 wherein optimizing a radiation-treatment plan to provide an initially-optimized radiation-treatment plan comprises optimizing the radiation-treatment plan without considering monitor units associated with the radiation-treatment plan.

3. The method of claim 1 wherein modifying the initially-optimized radiation-treatment plan to reduce monitor units comprises using an objective function.

4. The method of claim 3 wherein using an objective function comprises, at least in part, comparing an objective function result for a modified radiation-treatment plan against an objective function result for the initially-optimized radiation-treatment plan.

5. The method of claim 3 wherein using an objective function comprises, at least in part, calculating a threshold limit based upon an objective function result as corresponds to the initially-optimized radiation-treatment plan.

6. The method of claim 1 wherein modifying the initially-optimized radiation-treatment plan to reduce monitor units comprises, at least in part, imposing a stronger smoothing constraint with respect to fluence than was used to optimize the radiation-treatment plan to provide the initially-optimized radiation-treatment plan.

7. The method of claim 1 wherein identifying at least one particular leaf pair for a multi-leaf collimator that requires a longest amount of time to move into a position that achieves a particular desired fluence comprises identifying a subset of all leaf pairs of the multi-leaf collimator, which subset includes the leaf pairs that require the longest amounts of time to move as compared to other of the leaf pairs of the multi-leaf collimator.

8. An apparatus to facilitate optimizing a radiation-treatment plan, the apparatus comprising:
a control circuit configured to:
optimize a radiation-treatment plan to provide an initially-optimized radiation-treatment plan by, at least in part:
identifying at least one particular leaf pair for a multi-leaf collimator that requires a longest amount of time to move into a position that achieves a particular desired fluence; and
selectively smoothing position requirements of the particular leaf pair to reduce the amount of time associated with the particular leaf pair but not smoothing position requirements for all leaf pairs that comprise the multi-leaf collimator; and
modify the initially-optimized radiation-treatment plan to reduce monitor units to provide a radiation-treatment plan further optimized for monitor units.

9. The apparatus of claim 8 wherein the control circuit is configured to optimize the radiation-treatment plan to provide the initially-optimized radiation-treatment plan by optimizing the radiation-treatment plan without considering monitor units associated with the radiation-treatment plan.

10. The apparatus of claim 8 wherein the control circuit is configured to modify the initially-optimized radiation-treatment plan to reduce the monitor units by using an objective function.

11. The apparatus of claim 10 wherein the control circuit is configured to use the objective function by, at least in part, comparing an objective function result for a modified radiation-treatment plan against an objective function result for the initially-optimized radiation-treatment plan.

12. The apparatus of claim 10 wherein the control circuit is configured to use the objective function by, at least in part, calculating a threshold limit based upon an objective function result as corresponds to the initially-optimized radiation-treatment plan.

13. The apparatus of claim 8 wherein the control circuit is configured to modify the initially-optimized radiation-treatment plan to reduce the monitor units by, at least in part, imposing a stronger smoothing constraint with respect to fluence than was used to optimize the radiation-treatment plan to provide the initially-optimized radiation-treatment plan.

14. The apparatus of claim 8 wherein the control circuit is configured to identify the at least one particular leaf pair for a multi-leaf collimator that requires a longest amount of time to move into a position that achieves a particular desired fluence by identifying a subset of all leaf pairs of the multi-leaf collimator, which subset includes the leaf pairs that require the longest amounts of time to move as compared to other of the leaf pairs of the multi-leaf collimator.

15. A method to facilitate optimizing a radiation-treatment plan, the method comprising:
by a control circuit and while optimizing a radiation-treatment plan:
identifying at least one particular leaf pair for a multi-leaf collimator that requires a longest amount of time to move into a position that achieves a particular desired fluence;
selectively smoothing position requirements of the particular leaf pair to reduce the amount of time associated with the particular leaf pair but not smoothing position requirements for all leaf pairs that comprise the multi-leaf collimator.

16. The method of claim 15 wherein identifying at least one particular leaf pair for a multi-leaf collimator that requires a longest amount of time to move into a position that achieves a particular desired fluence comprises identifying a subset of all leaf pairs of the multi-leaf collimator, which subset includes the leaf pairs that require the longest amounts of time to move as compared to other of the leaf pairs of the multi-leaf collimator.

* * * * *